United States Patent
Oliver et al.

(10) Patent No.: US 9,969,784 B2
(45) Date of Patent: May 15, 2018

(54) COMPOSITIONS AND METHODS FOR MODULATION OF IMMUNE FUNCTION

(71) Applicant: THE CHILDREN'S HOSPITAL OF PHILADELPHIA, Philadelphia, PA (US)

(72) Inventors: Paula M. Oliver, Merion, PA (US); Christopher R. Riling, Exton, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 0 days. days.

(21) Appl. No.: 14/889,728

(22) PCT Filed: May 7, 2014

(86) PCT No.: PCT/US2014/037126
§ 371 (c)(1),
(2) Date: Nov. 6, 2015

(87) PCT Pub. No.: WO2014/182798
PCT Pub. Date: Nov. 13, 2014

(65) Prior Publication Data
US 2016/0122404 A1    May 5, 2016

Related U.S. Application Data

(60) Provisional application No. 61/820,678, filed on May 7, 2013.

(51) Int. Cl.
*A61K 38/00* (2006.01)
*C07K 14/47* (2006.01)
*A61K 9/127* (2006.01)
*A61K 38/17* (2006.01)
*A61K 45/06* (2006.01)
*G01N 33/573* (2006.01)

(52) U.S. Cl.
CPC .......... *C07K 14/4702* (2013.01); *A61K 9/127* (2013.01); *A61K 38/1709* (2013.01); *A61K 45/06* (2013.01); *C07K 14/47* (2013.01); *G01N 33/573* (2013.01); *G01N 2333/9015* (2013.01); *G01N 2500/20* (2013.01)

(58) Field of Classification Search
None
See application file for complete search history.

(56) References Cited

U.S. PATENT DOCUMENTS

2010/0135910 A1* 6/2010 Rao .................. C07K 16/40
424/9.2

OTHER PUBLICATIONS

Jolliffe, Biochem. J. (2000) 351, 557-565.*
Wang, 2010, JBC, 285, 12279-12288.*

* cited by examiner

*Primary Examiner* — Satyanarayana R Gudibande
(74) *Attorney, Agent, or Firm* — Kathleen D. Rigaut; Dann, Dorfman, Herrell & Skillman

(57) ABSTRACT

Compositions and methods for modulating immune cell function and Nedd-4 family member signaling are disclosed.

8 Claims, 7 Drawing Sheets

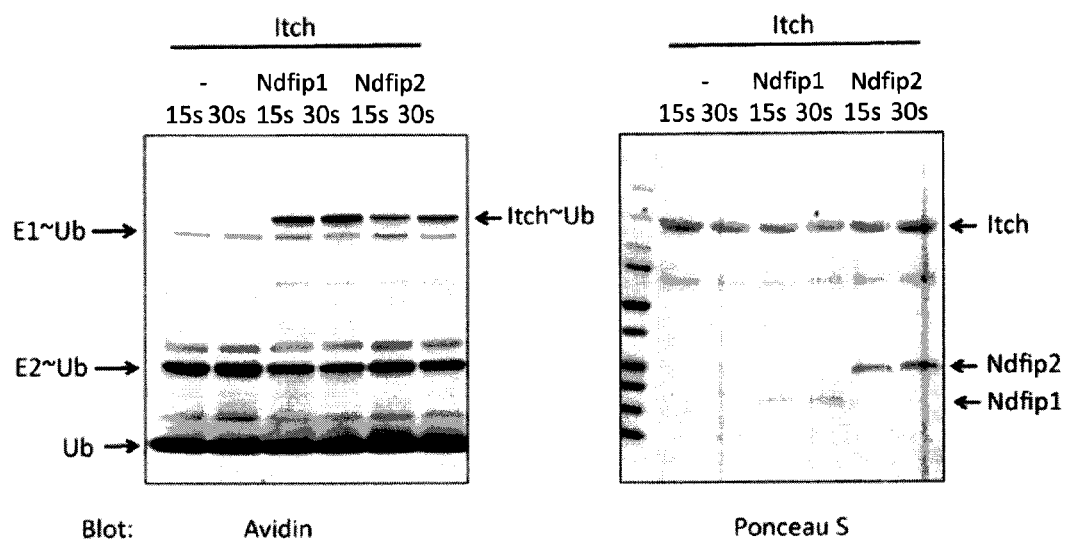
FIG. 1A  FIG. 1B
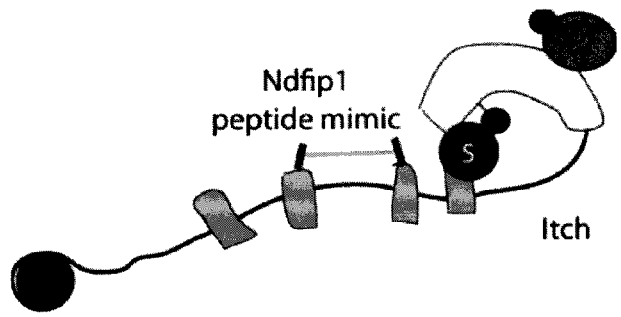
FIG. 1C
FIG. 1D

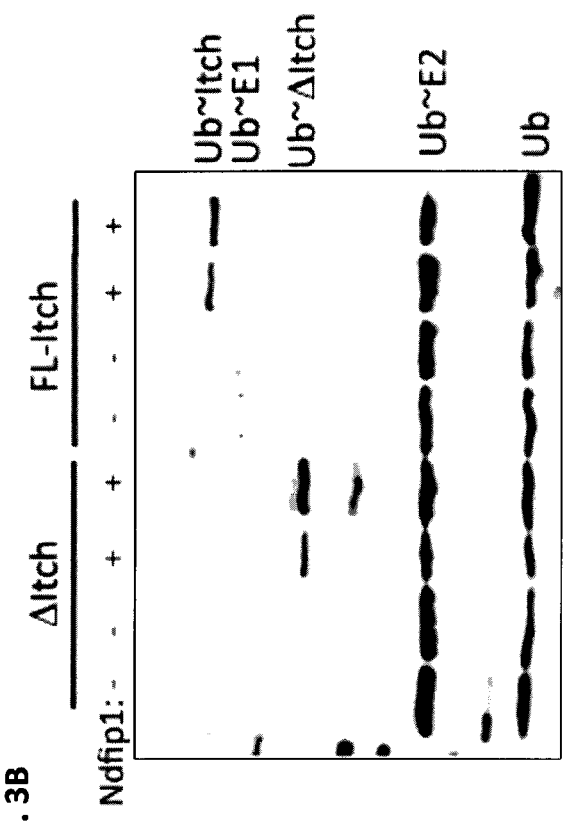
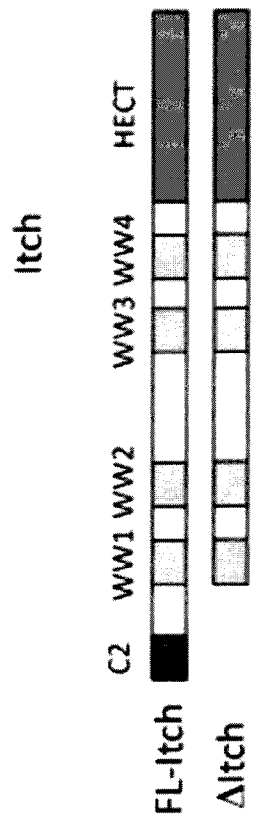
FIG. 3A
FIG. 3B

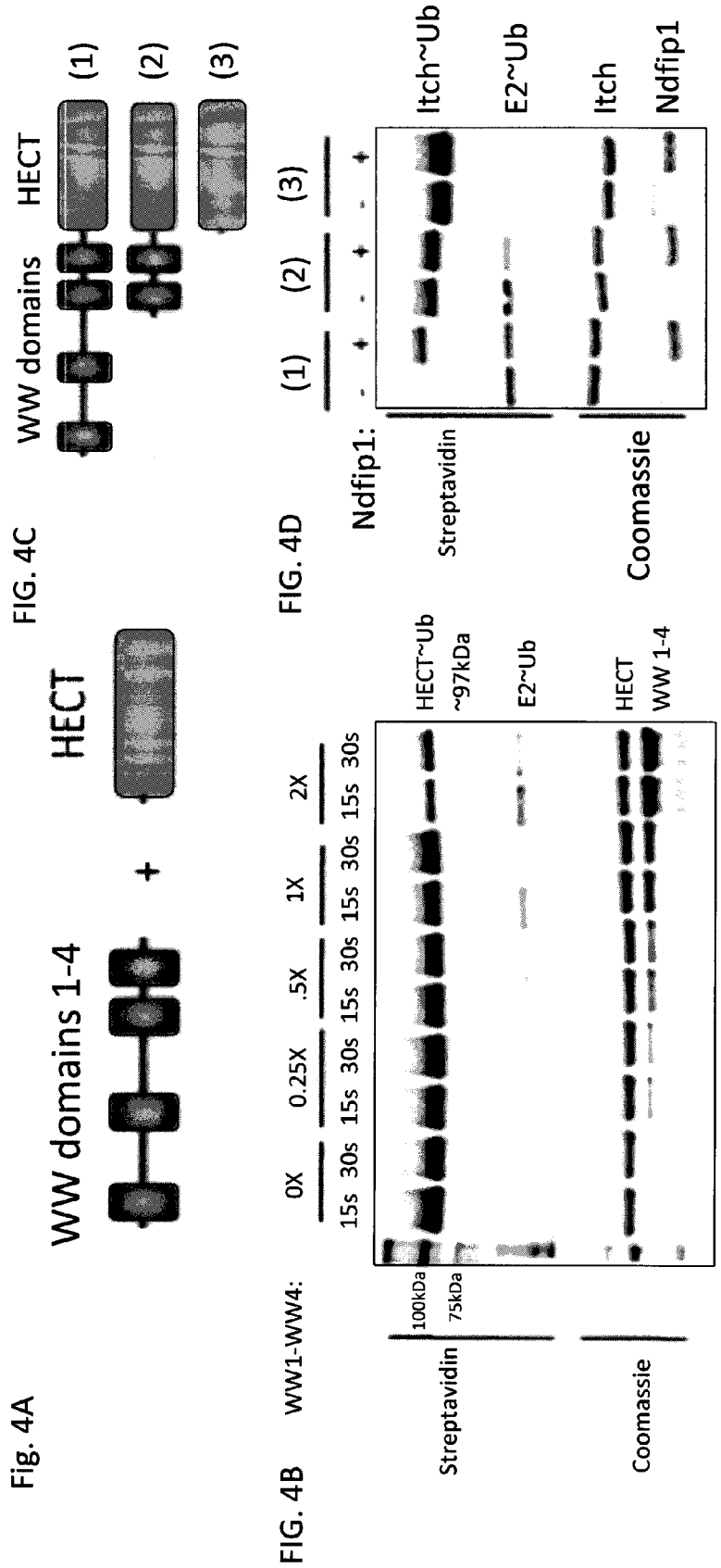

Alignment of HECT domain LPXY motifs
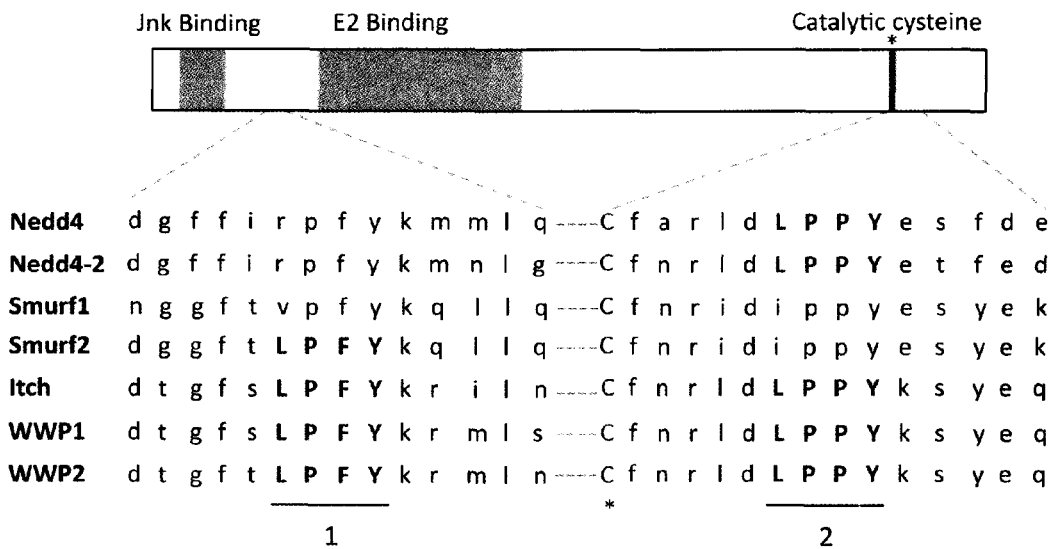
Figure 5
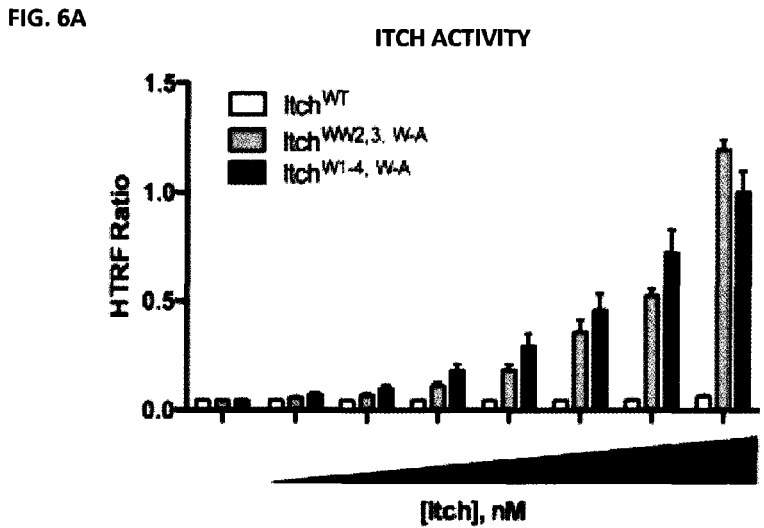
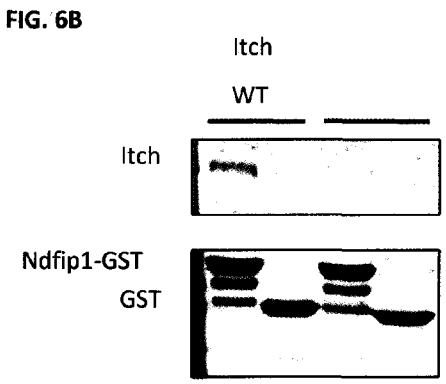
Figure 6

SEQUENCE LISTING

<160> NUMBER OF SEQ ID NOS: 22

<210> SEQ ID NO 1
<211> LENGTH: 25
<212> TYPE: PRT
<213> ORGANISM: Artificial Sequence
<220> FEATURE:
<223> OTHER INFORMATION: Synthetic peptide

<400> SEQUENCE: 1

Pro Glu Gln Thr Ala Gly Asp Ala Pro Pro Tyr Ser Ser Ile Thr
 1               5                  10                  15

Ala Glu Ser Ala Ala Tyr Phe Asp Tyr
            20                  25

<210> SEQ ID NO 2
<211> LENGTH: 35
<212> TYPE: PRT
<213> ORGANISM: Artificial Sequence
<220> FEATURE:
<223> OTHER INFORMATION: Synthetic peptide

<400> SEQUENCE: 2

Gly Asp Ala Pro Pro Tyr Ser Ser Ile Thr Ala Glu Ser Ala Ala
 1               5                  10                  15

Tyr Phe Asp Tyr Lys Asp Glu Ser Gly Phe Pro Lys Pro Pro Ser Tyr
            20                  25                  30

Asn Val Ala
        35

<210> SEQ ID NO 3
<211> LENGTH: 45
<212> TYPE: PRT
<213> ORGANISM: Artificial Sequence
<220> FEATURE:
<223> OTHER INFORMATION: Synthetic peptide

<400> SEQUENCE: 3

Gly Asp Ala Pro Pro Tyr Ser Ser Ile Thr Ala Glu Ser Ala Ala
 1               5                  10                  15

Tyr Phe Asp Tyr Lys Asp Glu Ser Gly Phe Pro Lys Pro Pro Ser Tyr
            20                  25                  30

Asn Val Ala Thr Thr Leu Pro Ser Tyr Asp Glu Ala Glu
        35                  40                  45

<210> SEQ ID NO 4
<211> LENGTH: 14
<212> TYPE: PRT
<213> ORGANISM: Artificial Sequence
<220> FEATURE:
<223> OTHER INFORMATION: Nedd4 PY motif

<400> SEQUENCE: 4

Asp Gly Phe Phe Ile Arg Pro Phe Tyr Lys Met Met Leu Gln
 1               5                  10

<210> SEQ ID NO 5
<211> LENGTH: 14
<212> TYPE: PRT
<213> ORGANISM: Artificial Sequence
<220> FEATURE:
<223> OTHER INFORMATION: Nedd4-2 PY motif

<400> SEQUENCE: 5

Asp Gly Phe Phe Ile Arg Pro Phe Tyr Lys Met Asn Leu Gly
 1               5                  10

<210> SEQ ID NO 6
<211> LENGTH: 14
<212> TYPE: PRT
<213> ORGANISM: Artificial Sequence
<220> FEATURE:
<223> OTHER INFORMATION: Smurf1 PY motif

<400> SEQUENCE: 6

Asn Gly Gly Phe Thr Val Pro Phe Tyr Lys Gln Leu Leu Gln
 1               5                  10

<210> SEQ ID NO 7
<211> LENGTH: 14
<212> TYPE: PRT
<213> ORGANISM: Artificial Sequence
<220> FEATURE:
<223> OTHER INFORMATION: Smurf2 PY motif

<400> SEQUENCE: 7

Asp Gly Gly Phe Thr Leu Pro Phe Tyr Lys Gln Leu Leu Gln
 1               5                  10

<210> SEQ ID NO 8
<211> LENGTH: 14
<212> TYPE: PRT
<213> ORGANISM: Artificial Sequence
<220> FEATURE:
<223> OTHER INFORMATION: Itch PY motif

<400> SEQUENCE: 8

Asp Thr Gly Phe Ser Leu Pro Phe Tyr Lys Arg Ile Leu Asn
 1               5                  10

<210> SEQ ID NO 9
<211> LENGTH: 14
<212> TYPE: PRT
<213> ORGANISM: Artificial Sequence
<220> FEATURE:
<223> OTHER INFORMATION: WWP1 PY motif

<400> SEQUENCE: 9

Asp Thr Gly Phe Ser Leu Pro Phe Tyr Lys Arg Met Leu Ser
 1               5                  10

<210> SEQ ID NO 10
<211> LENGTH: 14
<212> TYPE: PRT
<213> ORGANISM: Artificial Sequence
<220> FEATURE:
<223> OTHER INFORMATION: WWP2 PY motif

<400> SEQUENCE: 10

Asp Thr Gly Phe Thr Leu Pro Phe Tyr Lys Arg Met Leu Asn
 1               5                  10

<210> SEQ ID NO 11
<211> LENGTH: 15
<212> TYPE: PRT
<213> ORGANISM: Artificial Sequence
<220> FEATURE:
<223> OTHER INFORMATION: Nedd4 PY motif

<400> SEQUENCE: 11

Cys Phe Ala Arg Leu Asp Leu Pro Pro Tyr Glu Ser Phe Asp Glu

```
                1               5                  10                  15
```

<210> SEQ ID NO 12
<211> LENGTH: 15
<212> TYPE: PRT
<213> ORGANISM: Artificial Sequence
<220> FEATURE:
<223> OTHER INFORMATION: Nedd4-2 PY motif

<400> SEQUENCE: 12

```
Cys Phe Asn Arg Leu Asp Leu Pro Pro Tyr Glu Thr Phe Glu Asp
1               5                  10                  15
```

<210> SEQ ID NO 13
<211> LENGTH: 15
<212> TYPE: PRT
<213> ORGANISM: Artificial Sequence
<220> FEATURE:
<223> OTHER INFORMATION: Smurf1 PY motif

<400> SEQUENCE: 13

```
Cys Phe Asn Arg Ile Asp Ile Pro Pro Tyr Glu Ser Tyr Glu Lys
1               5                  10                  15
```

<210> SEQ ID NO 14
<211> LENGTH: 15
<212> TYPE: PRT
<213> ORGANISM: Artificial Sequence
<220> FEATURE:
<223> OTHER INFORMATION: Smurf2 PY motif

<400> SEQUENCE: 14

```
Cys Phe Asn Arg Ile Asp Ile Pro Pro Tyr Glu Ser Tyr Glu Lys
1               5                  10                  15
```

<210> SEQ ID NO 15
<211> LENGTH: 15
<212> TYPE: PRT
<213> ORGANISM: Artificial Sequence
<220> FEATURE:
<223> OTHER INFORMATION: Itch PY motif

<400> SEQUENCE: 15

```
Cys Phe Asn Arg Leu Asp Leu Pro Pro Tyr Lys Ser Tyr Glu Gln
1               5                  10                  15
```

<210> SEQ ID NO 16
<211> LENGTH: 15
<212> TYPE: PRT
<213> ORGANISM: Artificial Sequence
<220> FEATURE:
<223> OTHER INFORMATION: WWP1 PY motif

<400> SEQUENCE: 16

```
Cys Phe Asn Arg Leu Asp Leu Pro Pro Tyr Lys Ser Tyr Glu Gln
1               5                  10                  15
```

<210> SEQ ID NO 17
<211> LENGTH: 15
<212> TYPE: PRT
<213> ORGANISM: Artificial Sequence
<220> FEATURE:
<223> OTHER INFORMATION: WWP2 PY motif

<400> SEQUENCE: 17

```
Cys Phe Asn Arg Leu Asp Leu Pro Pro Tyr Lys Ser Tyr Glu Gln
1               5                  10                  15
```

<210> SEQ ID NO 18
<211> LENGTH: 4
<212> TYPE: PRT
<213> ORGANISM: Artificial Sequence
<220> FEATURE:
<223> OTHER INFORMATION: motif

<400> SEQUENCE: 18

Pro Pro Pro Tyr
 1

<210> SEQ ID NO 19
<211> LENGTH: 4
<212> TYPE: PRT
<213> ORGANISM: Artificial Sequence
<220> FEATURE:
<223> OTHER INFORMATION: motif

<400> SEQUENCE: 19

Pro Pro Ser Tyr
 1

<210> SEQ ID NO 20
<211> LENGTH: 4
<212> TYPE: PRT
<213> ORGANISM: Artificial Sequence
<220> FEATURE:
<223> OTHER INFORMATION: motif

<400> SEQUENCE: 20

Leu Pro Thr Tyr
 1

<210> SEQ ID NO 21
<211> LENGTH: 4
<212> TYPE: PRT
<213> ORGANISM: Artificial Sequence
<220> FEATURE:
<223> OTHER INFORMATION: motif
<220> FEATURE:
<221> NAME/KEY: VARIANT
<222> LOCATION: 3
<223> OTHER INFORMATION: Xaa = any amino acid

<400> SEQUENCE: 21

Leu Pro Xaa Tyr
 1

<210> SEQ ID NO 22
<211> LENGTH: 4
<212> TYPE: PRT
<213> ORGANISM: Artificial Sequence
<220> FEATURE:
<223> OTHER INFORMATION: motif
<220> FEATURE:
<221> NAME/KEY: VARIANT
<222> LOCATION: 1
<223> OTHER INFORMATION: Xaa = Leu or Pro
<220> FEATURE:
<221> NAME/KEY: VARIANT
<222> LOCATION: 3
<223> OTHER INFORMATION: Xaa = any amino acid

<400> SEQUENCE: 22

Xaa Pro Xaa Tyr
 1

COMPOSITIONS AND METHODS FOR MODULATION OF IMMUNE FUNCTION

This application is a § 371 application of PCT/US14/37126 filed May 7, 2014 which in turn claims priority to U.S. Provisional Application No. 61/829,678 filed May 7, 2013, the entire disclosure being incorporated herein by reference as though set forth in full.

This invention was made with government support under Grant Number, NIH R01 A1080765 awarded by the National Institutes of Health. The government has certain rights in the invention.

FIELD OF THE INVENTION

The present invention relates to the fields of protein processing and immune function. More specifically, the invention provides compositions and methods for activating or repressing Nedd4-family E3 ubiquitin ligase action as a means to improve immune function in subjects in need thereof.

BACKGROUND OF THE INVENTION

Several publications and patent documents are cited throughout the specification in order to describe the state of the art to which this invention pertains. Each of these citations is incorporated herein by reference as though set forth in full.

Nedd4-family E3 ubiquitin ligases regulate many biological processes including the sodium and iron homeostasis and inflammation. For example, the Nedd4-family members Itch can repress immune function in both innate and adaptive immune cells. Like other Nedd4-family members, Itch normally exists in an auto-inhibited state that prevents their main enzymatic task, transferring ubiquitin to a substrate protein. Thus, to pharmacologically harness Itch activity, one much first determine how auto-inhibition occurs and identify means to "de-repress" its catalytic activity.

SUMMARY OF THE INVENTION

In accordance with the present invention, a composition which relieves auto-inhibition of Itch or Nedd4-family members comprising similar motifs, comprising one or more peptides or variants thereof, selected from the group comprising 1) PEQTAGDAPPPYSSITAESAAYFDY (SEQ ID NO: 1); 2) GDAPPPYSSITAESAAYFDYKDESGFPK PPSYNVA (SEQ ID NO: 2); 3) GDA PPPYSSITAESAAYFDYKDESGFPK PPSYNVATTLPSYDEAE (SEQ ID NO: 3) in a pharmaceutically acceptable carrier, said peptide optionally being contained within a lipsome is provided. The liposomes may further comprise antibodies immunologically specific for molecules present on the surface of target cells to facilitate cellular uptake of the peptide. In a preferred embodiment, the peptides are contained within antibodies. In another embodiment, the peptides are operably linked to a cellular penetrating peptide.

In an alternative embodiment of the invention, a composition comprising a plurality of PPPY (SEQ ID NO: 18) or PPSY (SEQ ID NO: 19) peptide motifs operably linked via flexible linkers in a in a pharmaceutically acceptable carrier, said peptide optionally being contained within a liposome. In one embodiment two, three, four, five or more motifs are operably linked.

In yet another aspect of the invention, a method for reducing inflammation in a patient in need thereof is disclosed. An exemplary method entails administration of an effective amount of the compositions disclosed above which are effective to modulate T cell function in said patient, thereby reducing an undesired immune response. In another embodiment, the patient has a disorder selected from the group consisting of asthma, atopic dermatitis and inflammatory bowel disease.

BRIEF DESCRIPTION OF THE DRAWINGS

FIGS. 1A-1D. Ndfip1 and Ndfip2 promote ubiquitin charging of Itch. FIG. 1A: E1, E2, ubiquitin, ATP and Mg++ were incubated together to prepare the E2 for ubiquitin transfer. EDTA was added to prevent further transfer of ubiquitin from E1 to E2. This ensures that only a single ubiquitin will be transferred. Itch was then added to the reaction with or without Ndfip1 or Ndfip2. FIG. 1B: Ponceau S stain reveals protein loading for Itch, Ndfip1 and Ndfip2. FIG. 1C: Schematic diagram of auto-inhibition by Itch and activation by Ndfip1. FIG. 1D: Ndfip peptide mimics therapeutically activate FIGS. 2A-2B. Ndfip1 relies on PY motifs to promote Itch activation.

FIGS. 3A-3B. Itch auto-inhibition relies on HECT and WW domains. FIG. 3A: Itch and Ndfip1 constructs used in the assay in FIG. 3B. A full length Itch (FL-Itch) and a truncation mutant of Itch (ΔITCH) that lacks N-terminal regions including the C2 and proline rich motif were generated. FIG. 3B: These were analyzed in a ubiquitin charging assay in the presence or absence of Ndfip1.

FIGS. 4A-4D. Itch autoinhibition is due to an interaction between the HECT and WW domains. Constructs containing WW domain and HECT domain cassettes were generated as shown in FIGS. 4A and 4C. These were used in a ubiquitin charging assay in which equal amounts of the HECT motif were added to the assay with increasing concentrations of the WW domains (FIGS. 4B and 4D).

FIG. 5. Itch contains two PY motifs in Its HECT domain (LPXY, SEQ ID NO: 21). The sequences of Nedd4-family HECT domains were assessed to determine the source of auto-inhibition. A PY motif (1) was identified in the HECT-domain that is conserved in 4 of 7 Nedd4-family members (from top to bottom: SEQ ID NOs: 4-10). A second PY motif (2) was found several amino acids away from the catalytic cysteine in 5 of 7 members (from top to bottom: SEQ ID NOs: 11-17). NEDL1 and 2 lacked these motifs. Itch, and its most related family members WWP1 and WWP2, contain both PY motifs.

FIGS. 6A-6B. WW domains 2 and 3 dominate the Itch autoinhibitory interaction. FIG. 6A: A fret assay was used to determine which WW domains of Itch limited its activity. WW1-4A was used as a positive control. We found that a mutant of Itch with point mutations in WW domains 2 and 3 was active (not auto-inhibited) even in the absence of added Ndfip1. FIG. 6B: An Itch mutant with point mutations in WW2 and 3 was tested for its ability to bind Ndfip1, WT Itch was used as a positive control. Ndfip1 could not bind to Itch when it lacked functional WW2 and WW3 domains.

FIG. 7A: WT Itch and the WW2.3 mutant of Itch were transfected into Jurkat T cells. Itch and JunB stability was analyzed by western blot after stimulating cells in the presence or absence of cycloheximide (CHX). FIG. 7B: Itch stability was analyzed in 4 independent experiments and the combined data is shown. FIG. 7C: The impact of Itch levels on JunB stability is shown. The Itch WW2.3 mutant is illustrated by the closed circle. FIG. 7D: IL-2 reporter activity (tested using a luciferase assay) is shown. Based on these data, we conclude mutating the binding site in WW domains 2 and 3 makes Itch more active in vitro and reduces the stability of Itch.

DETAILED DESCRIPTION OF THE INVENTION

Figure 2A:
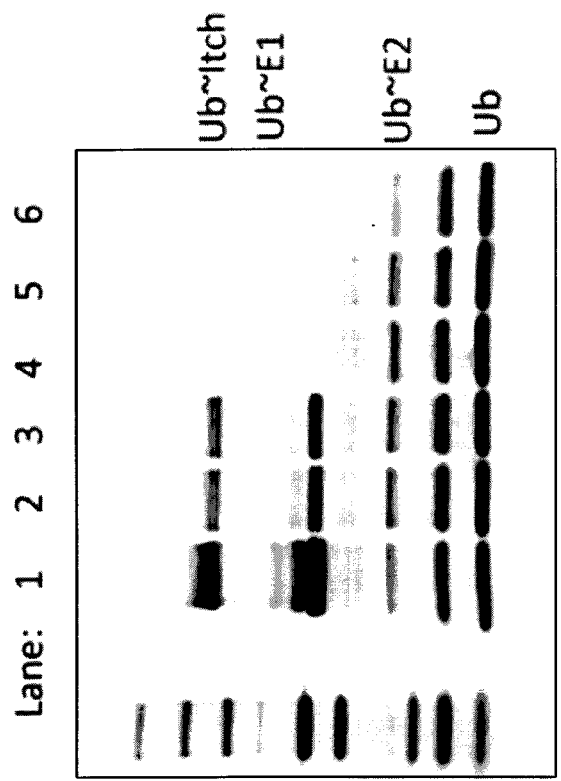
FIG. 2A: Itch and Ndfip1 constructs used in assay described in FIG. 2B. The Ndfip1 cytoplasmic domain, including its three PY motifs are shown fused to GST. Mutants of the PY motif are point mutations changing Y~>A. Itch charging was analyzed in the same assay as described in FIG. 1A, however in this case WT (lane 1) or PY mutants (lanes 2-5) of Ndfip1 were added. GST alone was added (lane 6) to assay Itch activity in the absence of Ndfip1.

In accordance with the present invention, we have now determined how auto-inhibition Itch is achieved. First, we determined that auto-inhibition does not affect Itch binding to an E2 ubiquitin conjugating enzyme but instead prevents the E2 from transferring ubiquitin to the catalytic cysteine residue in the Itch HECT domain, a process known as ubiquitin charging. As shown by our model in FIG. 1C, we have determined that Itch is autoinhibited due to an intramolecular interaction between its HECT and WW domains. It is worth noting that the motifs we have identified that mediate autoinhibition are conserved among other Nedd4-family members, suggesting that these discoveries can be extended to other Nedd4-family E3 ubiquitin ligases. Importantly, we have determined that Nedd4-family interacting protein 1 (Ndfip1) relieves Itch auto-inhibition (see FIG. 1C) by binding to the WW domains and releasing the HECT domain to allow ubiquitin charging. By doing this, Ndfip1 activates Itch to limit pro-inflammatory cytokine production in T cells and macrophages.

These discoveries provide guidance for the generation and testing of peptides that mimic Ndfip1. We demonstrate that these peptides activate Itch ubiquitin ligase activity in a cell free assay. Specifically, we have generated peptides that span one, two or all three of the motifs in Ndfip1 that bind WW domains of Itch. Addition of these peptides to our cell free assay resulted in the ubiquitin charging of Itch and thus Itch activation (modeled in FIG. 1D). Thus, we now have novel peptides that may be used to activate Itch and possibly other Nedd4-family E3 ubiquitin ligases for therapeutic purposes.

I. Definitions:

The phrase "immune related disorder" refers to disorders characterized by aberrant immune cell function mediated by T and B cells.

With reference to nucleic acids of the invention, the term "isolated nucleic acid" is sometimes used. This term, when applied to DNA, refers to a DNA molecule that is separated from sequences with which it is immediately contiguous (in the 5' and 3' directions) in the naturally occurring genome of the organism from which it originates. For example, the "isolated nucleic acid" may comprise a DNA or cDNA molecule inserted into a vector, such as a plasmid or virus vector, or integrated into the DNA of a prokaryote or eukaryote.

With respect to RNA molecules of the invention, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below).

With respect to protein, the term "isolated protein" or "isolated and purified protein" is sometimes used herein. This term refers primarily to a protein produced by expression of an isolated nucleic acid molecule of the invention. Alternatively, this term may refer to a protein which has been sufficiently separated from other proteins with which it would naturally be associated, so as to exist in "substantially pure" form.

The term "promoter region" refers to the transcriptional regulatory regions of a gene, which may be found at the 5' or 3' side of the coding region, or within the coding region, or within introns.

The term "vector" refers to a small carrier DNA molecule into which a DNA sequence can be inserted for introduction into a host cell where it will be replicated. An "expression vector" is a specialized vector that contains a gene or nucleic acid sequence with the necessary regulatory regions needed for expression in a host cell.

The term "operably linked" means that the regulatory sequences necessary for expression of a coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector. This definition is also sometimes applied to the arrangement of nucleic acid sequences of a first and a second nucleic acid molecule wherein a hybrid nucleic acid molecule is generated.

The term "substantially pure" refers to a preparation comprising at least 50-60% by weight the compound of interest (e.g., nucleic acid, oligonucleotide, protein, etc.). More preferably, the preparation comprises at least 75% by weight, and most preferably 90-99% by weight, of the compound of interest. Purity is measured by methods appropriate for the compound of interest (e.g. chromatographic methods, agarose or polyacrylamide gel electrophoresis, HPLC analysis, and the like).

The phrase "consisting essentially of" when referring to a particular nucleotide sequence or amino acid sequence means a sequence having the properties of a given SEQ ID NO:. For example, when used in reference to an amino acid sequence, the phrase includes the sequence per se and molecular modifications that would not affect the basic and novel characteristics of the sequence.

The term "oligonucleotide," as used herein refers to primers and probes of the present invention, and is defined as a nucleic acid molecule comprised of two or more ribo- or deoxyribonucleotides, preferably more than three. The exact size of the oligonucleotide will depend on various factors and on the particular application for which the oligonucleotide is used.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and method of use. For example, for diagnostic applications, depending on the complexity of the target sequence, the oligonucleotide probe typically contains 15-25 or more nucleotides, although it may contain fewer nucleotides.

The probes herein are selected to be "substantially" complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "specifically hybridize" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to act functionally as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product.

The primer may vary in length depending on the particular conditions and requirements of the application. For example, in diagnostic applications, the oligonucleotide primer is typically 15-25 or more nucleotides in length. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

The term "percent identical" is used herein with reference to comparisons among nucleic acid or amino acid sequences. Nucleic acid and amino acid sequences are often compared using computer programs that align sequences of nucleic or amino acids thus defining the differences between the two. For purposes of this invention comparisons of nucleic acid sequences are performed using the GCG Wisconsin Package version 9.1, available from the Genetics Computer Group in Madison, Wis. For convenience, the default parameters (gap creation penalty=12, gap extension penalty=4) specified by that program are intended for use herein to compare sequence identity. Alternately, the Blastn 2.0 program provided by the National Center for Biotechnology Information (on the world wide web at ncbi.nlm.nih.gov/blast/; Altschul et al., 1990, J Mol Biol 215:403-410) using a gapped alignment with default parameters, may be used to determine the level of identity and similarity between nucleic acid sequences and amino acid sequences.

II. Preparation of Polypeptides which Modulate Immune Cell Function

Nucleic acid molecules encoding the peptides of the invention may be prepared by using recombinant DNA technology methods. The availability of nucleotide sequence information enables preparation of isolated nucleic acid molecules of the invention by a variety of means. For example, nucleic acid sequences encoding an Itch modulating peptide may be isolated from appropriate biological sources using standard protocols well known in the art.

Nucleic acids of the present invention may be maintained as DNA in any convenient cloning vector. In a preferred embodiment, clones are maintained in a plasmid cloning/expression vector, such as pBluescript (Stratagene, La Jolla, Calif.), which is propagated in a suitable *E. coli* host cell. Alternatively, the nucleic acids may be maintained in vector suitable for expression in mammalian cells. In cases where post-translational modification affects immune function, it is preferable to express the molecule in mammalian cells.

B. Proteins

Polypeptides of the present invention may be prepared in a variety of ways, according to known methods. The protein may be purified from appropriate sources, e.g., transformed bacterial or animal cultured cells or tissues which express peptide encoding nucleic acids, by immunoaffinity purification. The availability of nucleic acid molecules encoding the inventive polypeptides enables production of the same using in vitro expression methods known in the art. For example, a cDNA or gene may be cloned into an appropriate in vitro transcription vector, such as pSP64 or pSP65 for in vitro transcription, followed by cell-free translation in a suitable cell-free translation system, such as wheat germ or rabbit reticulocyte lysates. In vitro transcription and translation systems are commercially available, e.g., from Promega Biotech, Madison, Wis. or BRL, Rockville, Md.

Alternatively, according to a preferred embodiment, larger quantities of peptide may be produced by expression in a suitable prokaryotic or eukaryotic expression system. For example, part or all of a DNA molecule encoding a peptide for example, may be inserted into a plasmid vector adapted for expression in a bacterial cell, such as *E. coli* or a mammalian cell such as CHO or Hela cells. Alternatively, in a preferred embodiment, tagged fusion proteins comprising the peptide can be generated. Such peptide-tagged fusion proteins are encoded by part or all of a DNA molecule, ligated in the correct codon reading frame to a nucleotide sequence encoding a portion or all of a desired polypeptide tag which is inserted into a plasmid vector adapted for expression in a bacterial cell, such as *E. coli* or a eukaryotic cell, such as, but not limited to, yeast and mammalian cells. Vectors such as those described above comprise the regulatory elements necessary for expression of the DNA in the host cell positioned in such a manner as to permit expression of the DNA in the host cell. Such regulatory elements required for expression include, but are not limited to, promoter sequences, transcription initiation sequences, and enhancer sequences.

The peptides of the invention, produced by gene expression in a recombinant prokaryotic or eukaryotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein or nickel columns for isolation of recombinant proteins tagged with 6-8 histidine residues at their N-terminus or C-terminus. Alternative tags may comprise the FLAG epitope, GST or the hemagglutinin epitope. Such methods are commonly used by skilled practitioners.

As discussed above, a convenient way of producing a polypeptide according to the present invention is to express nucleic acid encoding it, by use of the nucleic acid in an expression system. A variety of expression systems of utility for the methods of the present invention are well known to those of skill in the art.

Accordingly, the present invention also encompasses a method of making a polypeptide (as disclosed), the method including expression from nucleic acid encoding the polypeptide (generally nucleic acid). This may conveniently be achieved by culturing a host cell, containing such a vector, under appropriate conditions which cause or allow production of the polypeptide. Polypeptides may also be produced in in vitro systems, such as reticulocyte lysate.

III. Uses of Peptide Encoding Nucleic Acids and Proteins

Peptide encoding nucleic acids can be used to advantage to produce large quantities of the peptides disclosed herein. Alternatively, they may be inserted into expression vectors suitable for expression of the peptides in human subjects. Peptides produced thereby should be effective to modulate immune cell function in humans and may be used according to this invention, for example, as therapeutic and/or prophylactic agents which modulate T cell or B cell function. The present inventors have discovered that peptides which are effective to increase or repress Nedd4-family E3 ubiquitin ligase activity.

A. Polypeptides

The polypeptides may be used for a variety of purposes in accordance with the present invention. In a preferred embodiment of the present invention, the polypeptides may be administered to a patient via infusion in a biologically compatible carrier. The peptides of the invention may optionally be encapsulated in to liposomes or other phospholipids to increase stability of the molecule. Such liposomes may include an antibody targeting moiety, directing the peptides to a target cell of interest, such a B cell or T cell.

The peptides of the invention may be operably linked to a cellular penetrating peptide. Such peptides are known in the art and include the tat peptide and the MSP peptide. Other CPPs useful in the practice of the invention are disclosed in U.S. patent Ser. No. 13/264,482 which is incorporated herein by reference.

The peptides may be administered alone or in combination with other agents known to modulate immune function such as immunosuppressive agents or steroids. An appropriate composition in which to deliver the peptides may be determined by a medical practitioner upon consideration of a variety of physiological variables, including, but not limited to, the patient's condition and hemodynamic state. A variety of compositions well suited for different applications and routes of administration are well known in the art and described hereinbelow.

The preparation containing the purified peptide contains a physiologically acceptable matrix and is preferably formulated as a pharmaceutical preparation. The preparation can be formulated using substantially known prior art methods, it can be mixed with a buffer containing salts, such as NaCl, $CaCl_2$, and amino acids, such as glycine and/or lysine, and in a pH range from 6 to 8. Until needed, the purified preparation containing the peptide can be stored in the form of a finished solution or in lyophilized or deep-frozen form. Preferably the preparation is stored in lyophilized form and is dissolved into a visually clear solution using an appropriate reconstitution solution.

Alternatively, the preparation according to the present invention can also be made available as a liquid preparation or as a liquid that is deep-frozen.

The preparation according to the present invention is especially stable, i.e., it can be allowed to stand in dissolved form for a prolonged time prior to application.

The preparation according to the present invention can be made available as a pharmaceutical preparation with immune modulating activity in the form of a one-component preparation or in combination with other factors in the form of a multi-component preparation.

Prior to processing the purified protein into a pharmaceutical preparation, the purified peptide is subjected to the conventional quality controls and fashioned into a therapeutic form of presentation. In particular, during the recombinant manufacture, the purified preparation is tested for the absence of cellular nucleic acids as well as nucleic acids that are derived from the expression vector, preferably using a method, such as is described in EP 0 714 987.

Peptides useful in the practice of the invention, include for example,

```
                                          (SEQ ID NO: 1)
1) PEQTAGDAPPPYSSITAESAAYFDY (SEQ ID NO: 2)
2) GDAPPPYSSITAESAAYFDYKDESGFPKPPSYNVA (SEQ ID NO: 3)
3) GDAPPPYSSITAESAAYFDYKDESGFPKPPSYNVATTLPSYDEAE
```

The underlining indicates the motif that is known to bind Nedd4-family E3 ligases. Linked amino acid residues might be irrelevant. While all three of these peptides are effective to relieve Itch auto-inhibition, the minimal motif is predicted to be PPPY (SEQ ID NO: 18) or PPSY (SEQ ID NO: 19). Operably linking these two peptides via a flexible linker is predicted to be ideal. Removing lysine (K) residues from the sequence show in 1, 2 and 3 above, is predicted to stabilize the peptides in vivo. Accordingly, such variant peptides are also within the scope of the invention. Methods for modulating immune function include use of one, two or more of the peptide or peptide variants disclosed herein.

These peptides should decrease proinflammatory cytokine production in T cells and in macrophages, dendritic cells and other antigen presenting cells as well as in other innate inflammatory cells. Diseases that could be treated by such peptides include asthma, inflammatory bowel disease, food allergy, and atopic dermatitis. Psoriasis may also be improved by treatment with such peptides. While these peptides are based on sequence of Ndfip1, the peptide from Ndfip2 should also be effective and include the following sequences: PPPY (SEQ ID NO: 18) and LPTY (SEQ ID NO: 20). In this case, two peptides (i.e. PPPY (SEQ ID NO: 18) and LPTY (SEQ ID NO: 20) or two PPPY motifs) connected by a flexible linker should exhibit superior activity in vivo.

B. Pharmaceutical Compositions

Pharmaceutical preparations comprising the peptide in a suitable biological buffer may be administered to a patient via intravenous bolus infusion. The compositions may be administered alone or in combination with at least one other agent, such as a stabilizing compound, which may be administered in any sterile, biocompatible pharmaceutical carrier, including, but not limited to, saline, buffered saline, dextrose, and water. The compositions may be administered to a patient alone, or in combination with other agents which influence the inflammatory response.

In preferred embodiments, the pharmaceutical compositions also contain a pharmaceutically acceptable excipient. Such excipients include any pharmaceutical agent that does not itself induce an immune response harmful to the individual receiving the composition, and which may be administered without undue toxicity. Pharmaceutically acceptable excipients include, but are not limited to, liquids such as water, saline, glycerol, sugars and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in Remington's Pharmaceutical Sciences (Mack Pub. Co., 18th Edition, Easton, Pa. [1990]).

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art. The pharmaceutical compositions of the present invention may be manufactured in any manner known in the art (e.g., by means of conventional mixing, dissolving, granulating, dragee-making, levigating, emulsifying, encapsulating, entrapping, or lyophilizing processes).

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding, free base forms. In other cases, the preferred preparation may be a lyophilized powder which may contain any or all of the following: 1-50 mM histidine, 0.1%-2% sucrose, and 2-7% mannitol, at a pH range of 4.5 to 5.5, that is combined with buffer prior to use.

After pharmaceutical compositions have been prepared, they may be placed in an appropriate container and labeled for treatment. For administration of the peptides disclosed herein, such labeling would include amount, frequency, and method of administration.

Pharmaceutical compositions suitable for use in the invention include compositions wherein the active ingredients are contained in an effective amount to achieve the intended therapeutic purpose. Determining a therapeutically effective dose is well within the capability of a skilled medical practitioner using the techniques and guidance provided above. Therapeutic doses will depend on, among other factors, the age and general condition of the subject, the severity of the immune disorder, and the levels of peptide required. Thus, a therapeutically effective amount in humans will fall in a relatively broad range that may be determined by a medical practitioner based on the response of an individual patient to peptide treatment.

The following example is provided to illustrate certain embodiments of the invention. It is not intended to limit the invention in any way.

EXAMPLE I

Modulation of Nedd4-family E3 Ubiquitin Ligases as a Means to Regulate Immune Function E3 Ubiquitin ligases are essential in the regulation of many biological processes and have emerged as an exciting new class of "drugable" targets for pharmaceutical intervention. We recently discovered peptides which activate a class of E3 ubiquitin ligases thereby limiting pro-inflammatory cytokine production and inflammation. These peptides can be delivered to cells in vitro and in vivo and their effects on a reduction of the inflammatory response assessed. These agents may have particular utility for reducing inflammation in the gastrointestinal (GI) tract. The inventive peptides may also be useful for treating asthma, atopic dermatitis and other chronic inflammatory diseases.

We have determined how auto-inhibition of one Nedd4 family member is achieved and have identified the motifs which mediate auto-inhibition. Notably, these motifs are conserved among other family members. Accordingly, the peptides disclosed herein should have utility in modulating the function of most Nedd4-family E3 ubiquitin ligases. Additionally, we have identified a small family of adaptors, Ndfip1 and Ndfip2, that relieve auto inhibition and have determined how these adaptors work. This discovery has revealed novel peptides that may be used to activate Nedd4-family E3 ubiquitin ligases for therapeutic purposes. Additionally, these discoveries have revealed ways that small molecules could be used to promote or inhibit the function of Nedd4-family E3 ubiquitin ligases. Our studies have also revealed that in the absence of this regulatory mechanism, i.e. when the two adaptors are not expressed and thus cannot relieve auto-inhibition of Nedd4-family E3 ligases, overt inflammation develops leading to conditions that resemble, lympho-proliferation, asthma, atopic dermatitis and inflammatory bowel disease. Thus, therapeutic regulation of Nedd4-familyE3 ubiquitin ligases could be used to treat patients with these conditions.

Ndfip1 and Ndfip2 Relieve Auto-inhibition of the Nedd4-family E3 Ubiquitin Ligase Itch.

Figure 2B:
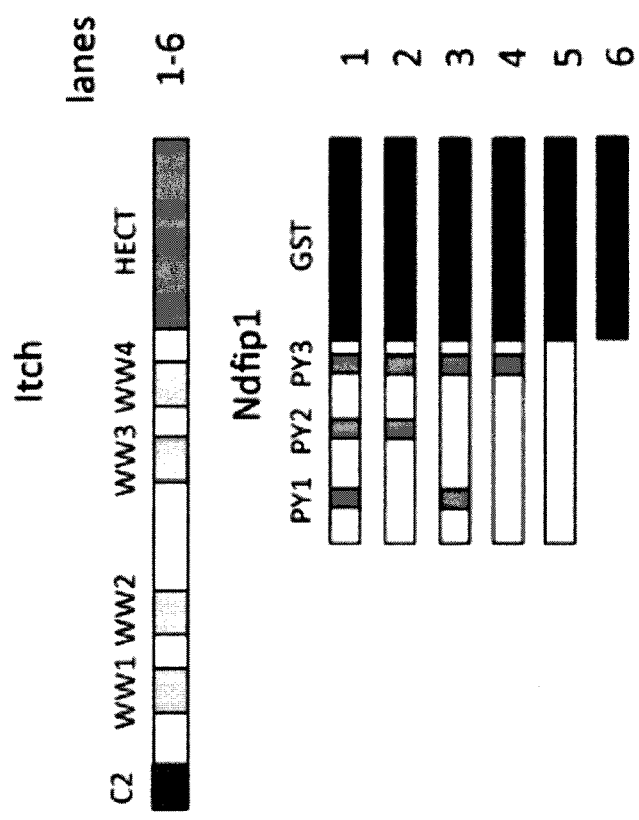
Figure 7C:
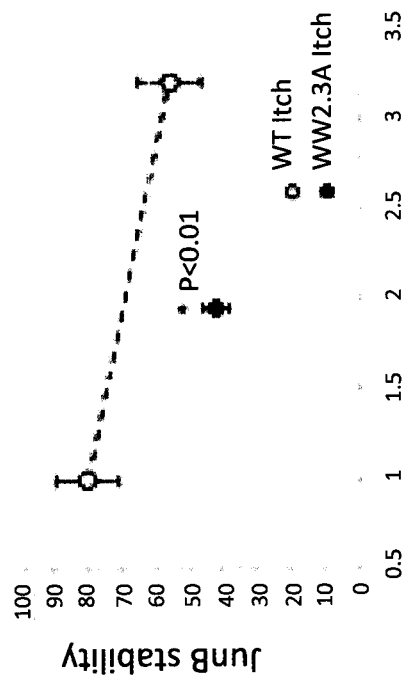
FIGS. 7A-7D. Itch activity increases when the protein is mutated in its WW domains.
Figure 7D:
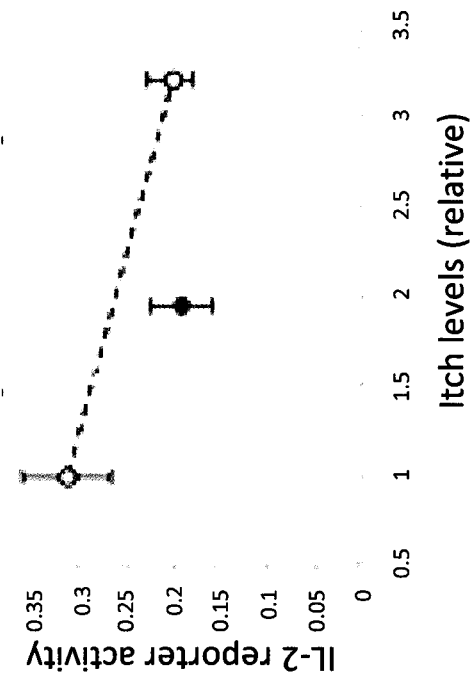
Figure 7A:
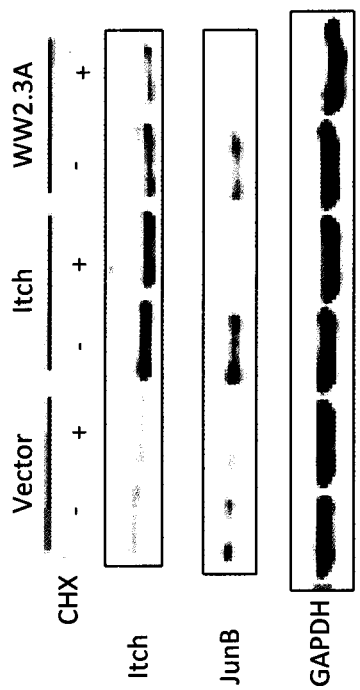
Figure 7B:
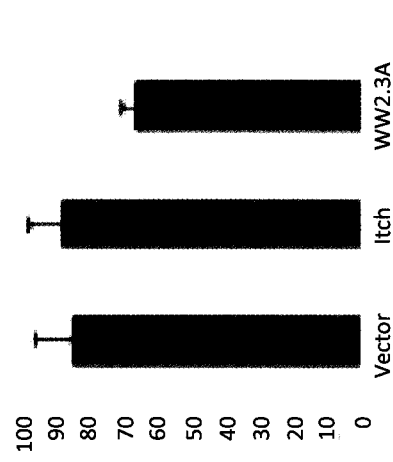
Figure 8:
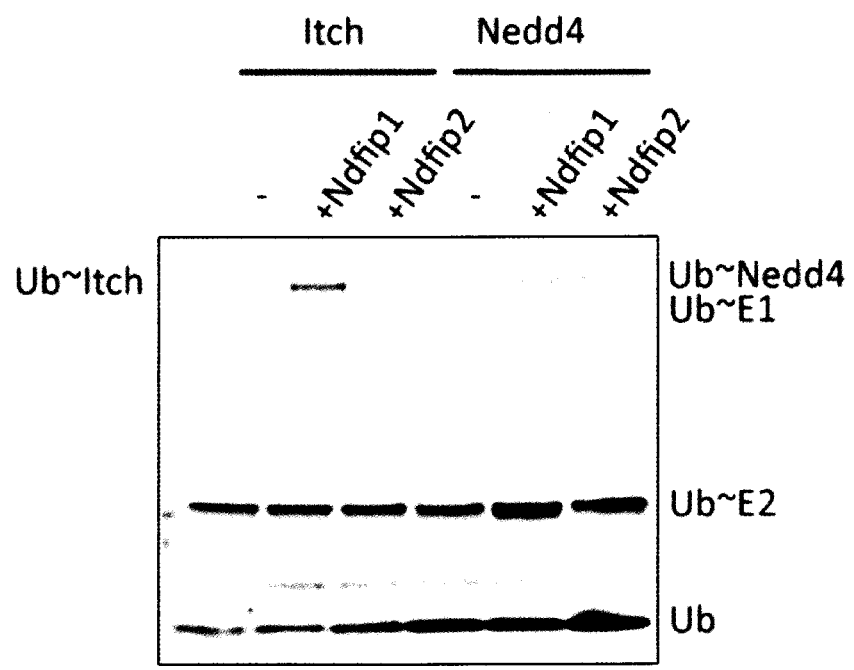
FIG. 8. Multiple Nedd4-family members likely share this mechanism of auto-inhibition and relief by Ndfip1 and Ndfip2. Nedd4 and Itch were expressed, purified and tested in the ubiquitin charging assay in the presence or absence of Ndfip1 or Ndfip2 as shown. Neither Itch nor Nedd4 were charged with ubiquitin in the assay when Ndfip1 or Ndfip2 were omitted from the assay. These assays were carried out for 30 seconds.

There are 9 members of the Nedd4-family of E3 ubiquitin ligases. These ligases are unusual in that there is a high degree of sequence similarity. All family members are composed of a HECT domain (the catalytic subunit), 2-4 WW domains, and a single C2 domain. Auto-inhibition of family members has been described by others, and different mechanisms of auto-inhibition have been proposed. For example, one family member, Itch, has been shown to be auto-inhibited due to an interaction between the HECT domain and a proline-rich region that sits between the C2 domain and the first WW domain (Gallagher, E et al. PMID 16446428). We have devised a new way to look at auto-inhibition, namely by using a ubiquitin charging assay which is the initial event in activating Nedd4-family E3 ubiquitin ligases. Ubiquitin charging occurs when an E2 ubiquitin conjugating enzyme transfers ubiquitin to the catalytic cysteine of the Nedd4-family E3 ligase. This event is absolutely required for catalytic activity of the E3 ligase. As shown in FIG. 2A, when Itch is added to this assay, there is no evidence of a band indicating ubiquitin charging of Itch, although bands indicating ubiquitin bound E1 and E2 are apparent. In contrast, when Ndfip1 or Ndfip2 are added, ubiquitin charging of Itch is observed. These data show that Ndfip1 and Ndfip2 promote the transfer of ubiquitin to the Itch catalytic cysteine, i.e., the initial event that results in Itch activation. We have determined that Ndfip1 and Ndfip2 are not required for Itch to bind the E2, as association between E2 and Itch occur in the absence of Ndfip1 and Ndfip2. E2-Itch binding occurs due to an interaction between the L1/PPXY (PY) motifs (SEQ ID NO: 22) of Ndfip1 and the WW domains of Itch. Thus, as shown in FIG. 2, when these PY motifs are missing, neither ubiquitin charging of Itch, nor Itch activation, occur.

Itch Auto-inhibition is Mediated by Intramolecular Interaction Between HECT and WW Domains.

Having determined that Ndfip1 promotes Itch activation, we decided to focus on how Itch autoinhibition works. We generated a truncation of Itch that contains only the HECT and WW domains and tested this in our ubiquitin charging assay. As seen in FIG. 3, Itch auto-inhibition occurs when Itch contains only these domains and this is still relieved by the addition of Ndfip1. Thus, we hypothesized that Itch inhibition is due to an intramolecular interaction between the HECT and WW domains.

To test this, we generated constructs that contain the WW domains (WW 1-4) and the HECT domain as separate cassettes. We then tested auto-inhibition of the HECT domain by adding the WW domains 'in trans'. Additionally, we truncated Itch so that it contained only 4, 2, or 0 WW domains. As seen in FIGS. 4C and D, as WW domains were removed, Itch auto-inhibition was relieved. FIG. 4 panel C shown the constructs containing 4, 2, or 0 WW domains. These were used in the ubiquitin charging assay described. Thus, Itch auto-inhibition is mediated by and interaction between its WW domains and its HECT domain.

Auto-Inhibition by this Mechanism is not Limited to Itch, but Rather May be Generalized to Multiple Nedd4-Family Members.

WW domains bind PY motifs as well as other motifs that are not well defined. Knowing that auto-inhibition of Itch is mediated by WW domain and HECT domain interactions, knowing that Ndfip1 binds to Itch via its PY motifs, and knowing that Ndfip1 relieves Itch auto-inhibition of Itch, we hypothesized that the Itch HECT motif might contain PY motifs. We thus surveyed the amino acid sequence or Itch for such motifs and identified two, noted PY1 and PY2 in FIG. 5.

Importantly, not only does Itch contain two such motifs in its HECT domain, but 6 out of 9 Nedd4-family members contain such motifs. Thus we have revealed a means of mediating auto-inhibition of multiple Nedd4-family members. Supporting this, we tested another Nedd4-family member, the prototypic member known as Nedd4. We found that, like Itch, Nedd4 was autoinhibited in the ubiquitin charging assay. Furthermore, this auto-inhibition was relieved by the addition of Ndfip1 or Ndfip2.

These data support that auto-inhibition of most Nedd4-family members is due to an interaction between the HECT and WW domains and that interaction with PY motif-containing adaptors is required for such auto-inhibition to be relieved. Based on these data, we propose that peptides that mimic Ndfip1 or Ndfip2 can be used to promote the activation of Nedd4 family E3 ligases.

In additional experiments, we introduced point mutations to destabilize the two WW domains and observed that Itch was significantly more active. This is most likely because Itch has lost its ability to form an autoinhibitory interaction between these domains and the HECT domain (FIG. 6a). Additionally, this mutant was no longer able to bind Ndfip1 (FIG. 6b).

We then tested whether this was important in vivo by expressing mutant and wild type Itch in human T cells (Jurkat). We found that Itch was much more active when it contained point mutations in WW domains 2 and 3 (FIG. 7). Increased Itch activity could be measured by increased degradation of JunB and reduced IL-2 production (two known measures of Itch function.

Mice Lacking Ndfip1 and Ndfip2 Expression Develop Inflammation at a Young Age and Die of Inflammatory Related Consequences Ndfip1 and Ndfip2 activate Nedd4-family E3 ubiquitin ligases, including Itch, to limit inflammation. Mice lacking Ndfip1 or both Ndfip1 and Ndfip2 develop conditions reminiscent of food allergy, asthma, atopic dermatitis, and inflammatory bowel disease. Our data support that Ndfip1 limits pro-inflammatory cytokines in both adaptive immune cells (T cells) as well as in innate immune cells. Thus peptides or small molecule approaches that relieve auto-inhibition of Itch or other Nedd4 family members should have utility for treatment of food allergy, asthma, atopic dermatitis and inflammatory bowel disease.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. An assay for identifying a polypeptide or mimic thereof which relieves auto-inhibition of a Nedd4-family member comprising a HECT domain and a WW domain, thereby increasing activation of Nedd4-family E3 ubiquitin ligase, comprising;
   a) incubating E1, E2, ubiquitin, ATP and Mg++ in a reaction mixture under conditions suitable for E2 ubiquitin conjugating enzyme to transfer ubiquitin to a catalytic cysteine of Nedd-4-family E3 ligase, said transfer being effective to activate said Nedd-4 family E3 ligase;
   b) adding a Nedd-4 family member to the reaction mixture of step a);
   c) determining the level of Nedd-4 family member activation in the presence of the polypeptide or mimic thereof, thereby identifying a small molecule polypeptide or mimic thereof that promotes ubiquitin transfer to said Nedd-4 family member, and relieves Nedd-4 family member auto-inhibition.

2. The assay of claim 1, wherein said Nedd-4 family member is Itch.

3. The assay of claim 1, wherein said peptide mimic is a of Nedd-4-family interacting protein 1 (Ndfip1) mimic and disrupts Nedd-4 family member WW and HECT domain interactions.

4. The assay of claim 1, wherein said polypeptide is Nedd-4-family interacting protein 2 (Ndfip2) or a peptide mimic thereof.

5. The assay of claim 4, wherein said Nedd-4-family member is Itch.

6. The assay of claim 1, wherein said peptide mimic comprises two or more PPPY (SEQ ID NO: 18) or PPSY (SEQ ID NO: 19) peptide motifs operably linked via a flexible linker.

7. The assay of claim 1, wherein said Nedd-4 family member is WWP1, WWP2 or Smurf2.

8. The assay of claim 1 wherein said polypeptide or mimic thereof is selected from the group consisting of:

(SEQ ID NO: 1)
1) PEQTAGDAPPPYSSITAESAAYFDY;

(SEQ ID NO: 2)
2) GDAPPYSSITAESAAYFDYKDESGFPKPPSYNVA; and (SEQ ID NO: 3)
3) GDAPPYSSITAESAAYFDYKDESGFPKPPSYNVATTLPSYDEAE.

* * * * *